United States Patent [19]

Dahlgren

[11] 4,076,733
[45] Feb. 28, 1978

[54] PROCESS FOR THE PREPARATION OF FURFURAL

[75] Inventor: Stig Åke Dahlgren, Lidingo, Sweden

[73] Assignee: Carbos AG, Zurich, Switzerland

[21] Appl. No.: 672,296

[22] Filed: Mar. 31, 1976

[51] Int. Cl.$^2$ .......................................... C07D 307/50
[52] U.S. Cl. .................................................. 260/347.9
[58] Field of Search ...................................... 260/347.9

[56] References Cited

U.S. PATENT DOCUMENTS

| 2,520,255 | 8/1950 | Peterman | 260/347.9 |
| 3,199,958 | 8/1965 | Skogh | 260/347.9 |

OTHER PUBLICATIONS

Morgan et al., J. of Dairy Science, vol. 140 (1957) pp. 571–578.
Dunlop et al., The Furans, New York–Reinhold (1953) pp. 277–283.
Jenness et al., Principles of Dairy Chemistry, New York, John Wiley (1959) pp. 83–85, 94–95, 354–355.
Gardner, J. Am. Chem. Soc. vol. 67 (1945) pp. 2111–2112.

Primary Examiner—Henry R. Jiles
Assistant Examiner—Bernard Dentz
Attorney, Agent, or Firm—Gordon W. Hueschen

[57] ABSTRACT

The invention relates to a process for the preparation of furfural from a carbohydrate, comprising subjecting a lactose-containing material to steam distillation, whereby at least part of the lactose present is converted to furfural.

13 Claims, No Drawings

PROCESS FOR THE PREPARATION OF FURFURAL

The present invention relates to an improved process for the preparation of furfural from carbohydrates by steam distillation.

Although the discovery of furfural dates back to the early half of the nineteenth century there was still in 1920 no commercial production of furfurl. By that time the Quaker Oats Company in 1922 started commercial production of furfural, the first important use thereof being for the production of phenol resins. Other uses were developed and the demands for furfural made necessary a considerable expansion in production capacity due to i.a. the synthetic rubber program during World War II.

Today furfural is commercially produced in great quantities, and pentosan-containing raw materials are used for such production. Typical raw materials are corn cobs, bagasse, peanut hulls and also to some extent birch wood. Corn cobs are an abundant source and this is the main raw material used in the production of furfural.

The manufacture of furfural is based on forming pentose from pentosan and water and hydrolyzing the pentose to yield furfural and water. Commercially, furfural is produced in a single-step operation. Basically, there are two different ways of producing furfural. In one process, the raw material is treated with dilute sulphuric acid. In another process, acidic conditions are formed in situ when using birch wood as a raw material. The acid conditions arising in the latter case are due to the formation of acetic acid.

In both processes, the furfural formed is removed by steam distillation. The vapours leaving the digesters are condensed and fed to a stripping column, where the overhead vapours, rich in furfural, are condensed and cooled and generally separated into two layers. The furfural layer containing about 6% water is sent to the dehydrating column, where the water is taken overhead and dry furfural is drawn from the base.

One drawback of the furfural production technique as described above is the fact that the raw materials used up to now contain a relatively low percentage of pentosans, which means tha enormous quantities of raw materials have to be handled and treated to obtain the desired quantities of furfural. Thus, the energy and apparatus requirements are extensive and result in relatively high production costs.

In accord with the instant invention, it has now surprisingly been found that, by using as a raw material a lactose-containing material, including lactose per se, furfural is obtained in a high yield. The lactose or lactose-containing material may be used as such or may be added to any other raw material of the conventional type, which results in a substantial increase in the yield of furfural.

The fact that lactose reacts in a manner to give furfural is in fact surprising, since as generally recognized lactose is a dihexose containing one galactose unit and one glucose unit. Generally, when treated with acid, hexoses do not form furfural but rather derivatives thereof in view of the presence of a sixth carbon atom. It was therefore highly surprising that steam distillation of lactoses resulted in the formation of furfural in high yield.

In general, the yield will be even better if the lactose is oxidized under mild conditions before or during the acid hydrolysis. Although the invention is not be be bound by any theory, the reason for the improved yield obtained by pre-oxidizing the lactose-containing material or the lactose per se may be the formation of a carboxyl group, which in turn splits off carbon dioxide to form a five-carbon atom carbohydrate, which then in turn hydrolyzes to furfural in high yields.

For oxidizing the lactose to improve the yield of furfural any oxidating agent capable of mild oxidation of organic compounds can be used, examples being bromine, aqueous hydrogen peroxide, dilute nitric acid, peracids, or the like. Among the peracids peracetic acid is preferred, although other peracids, such as perbenzoic and monoperphthalic, may also be used. It is immaterial whether the peracid is generated in situ by addition of hydrogen peroxide to the carboxylic acid, or if the peracid is preformed. The pre-oxidation is preferably performed at an increased temperature, such as up to about 80° C.

Any lactose-containing material can be used to form furfural according to the invention. Beside lactose per se, whey obtained from cheese production is an excellent raw material, the lactose preferably in such case being used in the form of an about twenty percent by weight concentrate of lactose in water. Such concentrate is readily obtained by removing the milk protein from the whey and concentrating the lactose solution thereby obtained. Generally, whey tends to constitute an environmental problem, since it is produced in great quantities in milk-treatment plants all over the world, no practical use of the whey having been found prior to the present invention.

The results of practical tests performed indicate that approximately half of the lactose molecule is converted in such a manner to give furfural but, under most favourable conditions, a major part of the lactose seems to be convertible into furfural. For maximum yield it is preferred to use an oxidating millieu under moderate acid conditions.

Accordingly, the main object of the invention is to provide a process for the preparation of furfural from lactose or a lactose-containing material by steam distillation alone or together with some other inexpensive raw material containing pentosans, for example of the type as indicated above in the introductory part of this specification.

Yet another object is to provide for a process whereby furfural is produced in an increased yield while facilitating the raw-material treatment and decreasing the energy requirements.

Still another object is to provide a process for the preparation of furfural, starting from a wood material resulting in per se production of acetic acid, with addition thereto of a lactose-containing material, either preceding or during the reaction but preferably also prior to commencement of steam distillation of the wood material.

A further object of the invention is to provide a process for the preparation of furfural by using a pre-oxidized lactose--containing material as a starting material.

The invention will now be further described by specific examples which, however, must not be construed to delimit the scope of the invention.

In the following examples there is used a stainless steel reactor, to the bottom of which there is introduced steam having a pressure of about 12 atms and a temperature of about 186° C. The vapours leaving the reactor are transferred to a water-cooled condenser, the condensate from which is analyzed with regard to its content of furfural. The analysis is carried out with a gas chromatograph of the type Perkin Elmer, Model F17 (Perkin-Elmer Limited, England), pyridine in a known amount being added to the samples and used as a control reference. The raw materials may be introduced into the reactor through a removable upper end wall.

It is to be noted that the test reactor, used in performing the practical experiments as per the following examples, is operated in a batch-wise manner, the residual hydrolystate being removed after each test. In each test the steam treatment had a duration of 1 hour and 45 minutes, during which period the vapours leaving the reactor were condensed and collected for gas chromatography to determine the furfural content of the condensate.

EXAMPLE 1

5000 g of birch wood chips, having a dry solids content of 2690 g, are supplied to the reactor and treated in the manner indicated above. The condensate is analyzed by gas chromatography with regard to its content of furfural, the yield of furfural being 4.8% by weight on a dry basis of the birch wood. This test is used as a control test.

EXAMPLE 2

Birch wood chips in the same amount and of the same type as in Example 1 are supplied to the test reactor together with 200 g of whey lactose in powder form. Said materials are subjected to the same treatment as in Example 1, and upon analyzing the condensate the yield of furfural is found to be 6.7% by weight on the same basis.

EXAMPLE 3

The procedure in Example 2 above is repeated, but in this case 170 ml aqueous 35% hydrogen peroxide solution are also added to the reactor before the steam treatment. The yield of furfural is 7.82% by weight on the same basis.

From the above examples it can readily be seen how the lactose addition contributes to the yield of furfural. It must, however, be noted that the basic furfural yield as per Example 1 above does not reflect the true yield in a continuous process for the preparation of furfural, since the acetic acid level of the test reactor starts at zero, whereas in a continuous process the acetic acid level builds up and becomes constant at a certain level, which is favourable for a high furfural yield. Therefore, in order to simulate the conditions of a continuous process, further experiments were performed as follows.

EXAMPLE 4

The procedure of Example 1 is repeated while adding also 125 ml of glacial acetic acid to the reactor before closing same. The yield of furfural is 8.4% by weight on a dry basis of the birch wood.

EXAMPLE 5

Now Example 2 is repeated while adding the same amount of glacial acetic acid as per Example 4. The yield of furfural is 10.2% by weight on the same basis.

EXAMPLE 6

The procedure of Example 1 is repeated while adding also 50 ml of concentrated sulfuric acid to the reactor before closing same. The yield of furfural is 8.7 percent by weight on a dry basis of the birch wood.

EXAMPLE 7

Now Example 2 is repeated while adding the same amount of concentrated sulfuric acid as per Example 6. The yield of furfural is 10.5% by weight on the same basis.

EXAMPLE 8

The procedure of Example 3 is repeated while adding also 125 ml of glacial acetic acid to the reactor before closing same. The yield of furfural is 10.9% by weight on a dry basis of the birch wood.

EXAMPLE 9

The procedure of Example 3 is repeated while adding also 50 ml of concentrated sulfuric acid to the reactor before closing same. The yield of furfural is 11.1% by weight on a dry basis of the birch wood.

It is clear from the above examples that steam distillation under oxidizing conditions is favourable with regard to the overall yield of furfural. It is also clear from Examples 4 to 9 that the presence of an acid is favourable to the yield of furfural.

As has been indicated earlier in this specification, whey is an abundant material found in all milk-producing spots of the world. Whey contains as major constituents lactose and protein, these constituents being separable by applying a so-called membrane technique. Up to the instant invention, lactose has not found any widespread use. Against this background this invention is of a far-reaching economical importance, since lactose may easily be added to the conventional raw materials in existing plants for furfural production resulting in an improved capacity of the plant without significantly increased raw material cost. The lactose may be added in the form of a dry powder but can also be added in the form of an aqueous concentrate, although in the latter case a somewhat increased steam consumption results.

It is to be understood that the invention is not delimited to the above examples which are based upon the use of birch wood chips as a basic furfural-producing raw material, and that it is equally applicable to all kinds of raw materials as indicated earlier in this specification. The process of the invention is thus useful also in connection with digestion and treatment in the presence of dilute sulphuric acid or other mineral acids which have been used previously for such type of production, albeit with somewhat lesser degree of economic advantage.

It is to be understood that the invention is not to be limited to the exact details of operation or exact compounds, compositions, methods, or procedures shown and described, as many modifications and equivalents of the process illustrated in the foregoing will be apparent to one skilled in the art and may be in the method and procedure of the present invention without departing from the spirit or scope thereof.

What is claimed is:

1. A process for the preparation of furfural comprising subjecting a lactose-containing material essentially free of milk proteins to steam distillation under acidic conditions, whereby at least part of the lactose present is converted to furfural.

2. A process according to claim 1, in which the acidic conditions are due to a non-oxidizing acid at least as strong as acetic acid.

3. The process of claim 2, in which the acid is sulfuric acid or acetic acid.

4. The process of claim 2, in which the lactose-containing material comprises a whey concentrate from which the milk proteins have been removed.

5. The process of claim 4, in which the acid is sulfuric acid or acetic acid.

6. In a process for the preparation of furfural from a pentosan-containing raw material by steam distillation under acid conditions, the improvement comprising adding to said raw material a lactose-containing material which is essentially free of milk proteins whereby the yield of furfural in the vapours distilled ooff is substantially increased.

7. The process of claim 6, in which the acid conditions are due to a non-oxidizing acid at least as strong as acetic acid.

8. The process of claim 7, in which the acid is sulfuric acid or acetic acid.

9. The process of claim 6, in which the lactose-containing material comprises a whey concentrate from which the milk proteins have been removed.

10. The process of claim 10, in which the pentosan-containing raw material comprises birch wood bark and the acid comprises acetic acid derived in the steam distillation from said birch bark.

11. A process according to claim 10, wherein the lactose-containing material is added to the birch wood before supplying steam thereto.

12. The process of claim 10, in which sulfuric acid is added.

13. The process of claim 12, in which the lactose-containing material comprises a whey concentrate from which the milk proteins have been removed.

* * * * *

UNITED STATES PATENT OFFICE
CERTIFICATE OF CORRECTION

Patent No. 4,076,733  Dated Feb. 28, 1978

Inventor(s) Stig Ake Dahlgren

It is certified that error appears in the above-identified patent and that said Letters Patent are hereby corrected as shown below:

[75] Inventor : "Lidingo"  should read -- Lidingö --.
[56] Other Publications: "J. of Dairy Science, vol. 140" should read --J. of Dairy Science, vol. 40--
Col. 1, line 13: "phenol" should read --phenolic--
Col. 1, line 47: "tha" should read --that--
Col. 2, line 3: "be" (second occurrence) should read -- to --.
Col. 5, line 20: "ooff" should read --off--

Signed and Sealed this

Twenty-fifth Day of July 1978

[SEAL]

Attest:

RUTH C. MASON
Attesting Officer

DONALD W. BANNER
Commissioner of Patents and Trademarks

UNITED STATES PATENT OFFICE
CERTIFICATE OF CORRECTION

Patent No. 4,076,733  Dated February 28, 1978

Inventor(s) Stig Åke Dahlgren

It is certified that error appears in the above-identified patent and that said Letters Patent are hereby corrected as shown below:

On the title page item [56] Other Publications, "J. of Dairy Science, vol. 140" should read -- J. of Dairy Science, vol. 40 --.

Signed and Sealed this

Twenty-fourth Day of October 1978

[SEAL]

Attest:

RUTH C. MASON
Attesting Officer

DONALD W. BANNER
Commissioner of Patents and Trademarks